(12) United States Patent
Gershowitz

(10) Patent No.: US 6,913,597 B2
(45) Date of Patent: Jul. 5, 2005

(54) RETROGRADE CANNULA PREVENTING BLOOD BACK-FLOW DURING STYLET REMOVAL

(75) Inventor: Arthur D. Gershowitz, Ann Arbor, MI (US)

(73) Assignee: Terumo Cardiovascular Systems, Ann Arbor, MI (US)

( * ) Notice: Subject to any disclaimer, the term of this patent is extended or adjusted under 35 U.S.C. 154(b) by 129 days.

(21) Appl. No.: 10/082,119

(22) Filed: Feb. 26, 2002

(65) Prior Publication Data

US 2003/0163116 A1 Aug. 28, 2003

(51) Int. Cl.⁷ .................. A61M 25/00; A61M 37/00
(52) U.S. Cl. .................. 604/264; 604/103.11; 604/509
(58) Field of Search ............... 604/103–103.11, 604/509, 508, 264, 96.01, 912, 510, 507

(56) References Cited

U.S. PATENT DOCUMENTS

| 4,299,226 | A | * | 11/1981 | Banka | 604/509 |
| 4,919,651 | A | * | 4/1990 | Doane | 604/103.11 |
| 5,395,331 | A | * | 3/1995 | O'Neill et al. | 604/103.08 |
| 5,637,086 | A | * | 6/1997 | Ferguson et al. | 604/509 |
| 5,795,331 | A | * | 8/1998 | Cragg et al. | 604/103.01 |

* cited by examiner

Primary Examiner—Nicholas D. Lucchesi
Assistant Examiner—Roz Maiorino

(57) ABSTRACT

A retrograde cannula for delivering fluid to a human heart has proximal and distal ends and includes an infusion lumen adapted to conduct CPG for discharge into the heart. An expandable balloon is disposed adjacent the distal end of the cannula for receiving CPG which expands the balloon into sealing relationship with a wall of the heart. A stylet lumen extends adjacent to the infusion lumen for receiving a stylet. A distal end of the stylet lumen is blocked.

8 Claims, 5 Drawing Sheets

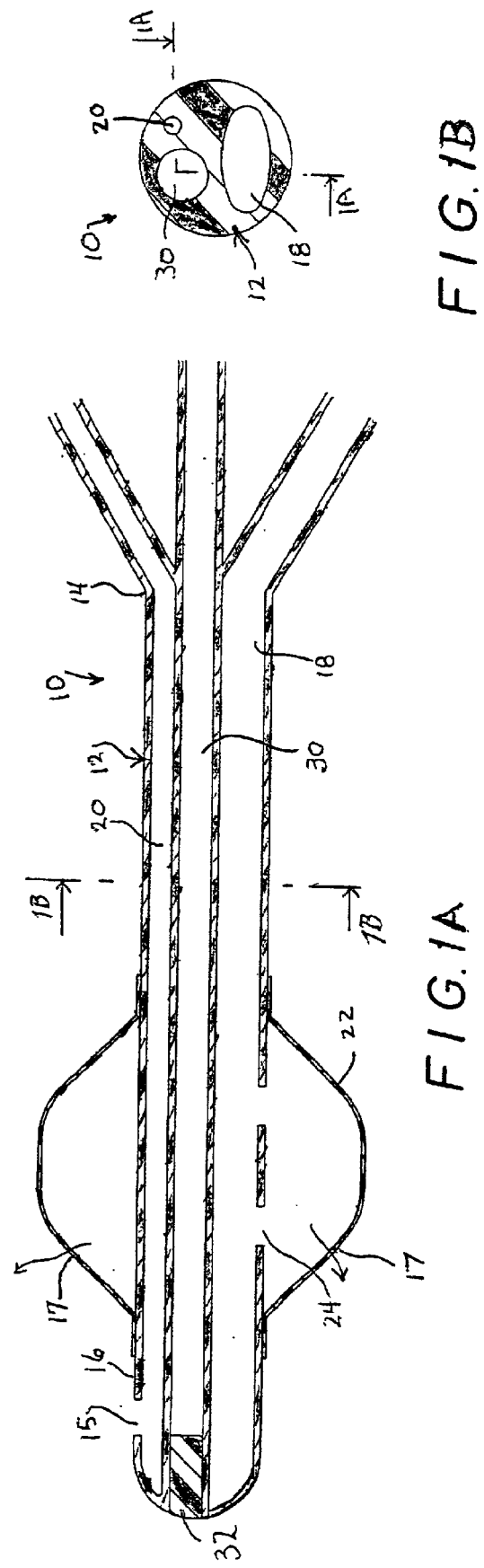

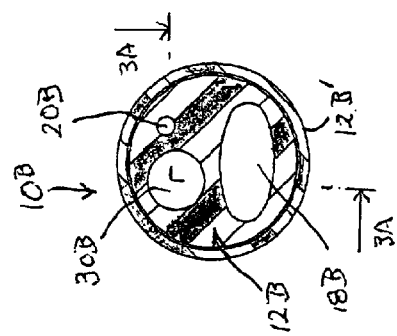
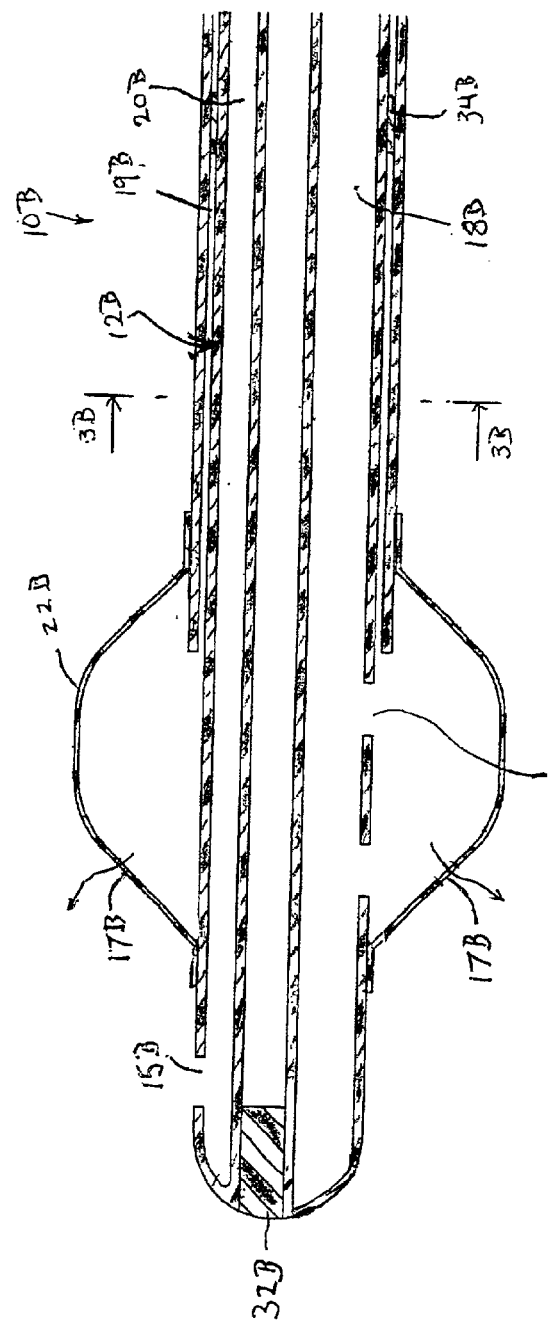
FIG. 3B
FIG. 3A

RETROGRADE CANNULA PREVENTING BLOOD BACK-FLOW DURING STYLET REMOVAL

BACKGROUND OF THE INVENTION

The present invention relates to balloon cannulas, and in particular to retrograde cannulas used in the delivery of cardioplegia.

Retrograde cannulas are commonly employed during certain cardiac surgical procedures, in order to deliver cardioplegia into coronary veins to effect cardiac arrest by depolarizing cell membranes (see U.S. Pat. No. 5,395,331).

A conventional retrograde cannula 100 is depicted in FIG. 5. In order to occlude the coronary sinus, the distal end 102 of the cannula 100 includes an inflatable balloon 104 which, when inflated, seals against a wall of the coronary sinus. Balloons may be of the manual-inflating or auto-inflating type. In the manual inflating type, fluid is supplied to or removed from the balloon by means of a syringe. In the auto-inflating type (also referred to as self-inflating), the balloon is in fluid communication with an infusion lumen through which is the CPG delivered to the blood stream, and is inflated by the CPG.

The cannula itself is highly flaccid and would be difficult to install in its normal flaccid state. Accordingly, it is conventional to insert a stylet 106 into the cannula to stiffen it. The stylet is inserted into the proximal end of an infusion lumen that is to be used to deliver the CPG to the patient via outlet 108. After the cannula has been installed, the stylet is removed so that CPG can be delivered through the infusion lumen. However, upon removal of the stylet, it is possible for there to occur a backflow of blood through the infusion lumen from its distal end to its proximal end, until the proximal end is closed off, e.g., by a clamp. The backflowing blood could potentially come into contact with surgical personnel, which is undesirable from a health safety standpoint.

Therefore, it would be desirable to provide a retrograde cannula which avoids a back-flow of blood when removing the stylet. Moreover, after the cannula has been inserted, it may become dislodged from its intended position, especially in the case of an auto-inflate cannula wherein the balloon becomes deflated when the delivery of CPG is halted, so that the distal end of the cannula is no longer supported. In order to reposition the cannula, it may be necessary to re-insert the stylet, which requires removal of a CPG-supply conduit attached to the infusion lumen.

Therefore, it would also be desirable to provide a retrograde cannula which avoids the need to disconnect a fluid supply conduit when re-inserting the stylet.

SUMMARY OF THE INVENTION

One aspect of the invention pertains to a retrograde cannula for delivering fluid to a patient's vessel. The cannula has proximal and distal ends and includes an infusion lumen for conducting fluid, such as CPG, which is to be discharged into the patient's vessel. The cannula further includes a stylet lumen extending adjacent to the infusion lumen for receiving a stylet. A distal end of the stylet lumen is blocked. The cannula further includes an expandable sealing member disposed adjacent to the distal end for being expanded into sealing relationship with a wall of the vessel.

Another aspect of the invention pertains to a method of infusing a vessel with fluid using a retrograde cannula. The method includes the steps of:

A) inserting a stylet into a stylet inlet of a lumen of a catheter body;

B) manipulating a handle of the stylet for introducing a distal end of the catheter body into the vessel;

C) removing the stylet from the catheter body through the stylet inlet;

D) conducting fluid through a fluid inlet of the lumen that is spaced from the stylet inlet; and E) discharging the fluid into the vessel.

BRIEF DESCRIPTION OF THE DRAWINGS

The objects and advantages of the invention will become apparent from the following detailed description of preferred embodiments thereof in connection with the accompanying drawings in which like numerals designate like elements and in which:

FIG. 1A is a longitudinal sectional view taken through a cannula along the line 1A—1A in FIG. 1B according to a first embodiment of the present invention.

FIG. 1B is a sectional view taken along the line 1B—1B in FIG. 1A.

FIG. 3A is a longitudinal sectional view taken through a cannula along the line 3A—3A in FIG. 3B according to a third embodiment of the present invention.

FIG. 3B is a cross sectional view taken along the line 3B—3B in FIG. 3A.

DETAILED DESCRIPTION OF PREFERRED EMBODIMENTS OF THE INVENTION

Figure 2B:
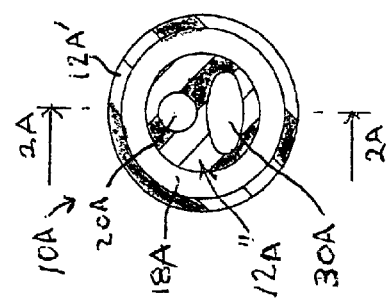
FIG. 2B is a sectional view taken along the line 2B—2B of FIG. 2A.

Depicted in FIGS. 1A and 1B is a first embodiment of a retrograde cannula 10 according to the present invention. The cannula includes a body 12 formed of a flexible plastic material suitable for insertion into a human body, such as PVC urethane or silicone. Extending through the body from a proximal end 14 to a distal end 16 thereof is an infusion lumen 18 capable of delivering fluid such as cardioplegia (CPG) to a heart vessel (e.g., coronary sinus).

Also extending through the body 12 is a pressure monitoring lumen 20 which has an opening 15 at its distal end to sense fluid pressure.

Disposed on the outer periphery of the body 12 adjacent the distal end thereof is an expandable sealing element, preferably in the form of an inflatable balloon 22. The infusion lumen 18 communicates with the balloon interior by way of communication holes 24 so that the balloon can be inflated by pressurized CPG being delivered to the vessel through the infusion lumen. The CPG then exits the balloon and enters the coronary sinus through openings 17 formed in a forward section of the balloon, as shown by the arrows in FIG. 1A.

A retrograde cannula similar to that described above is disclosed in U.S. Pat. No. 5,395,331. As pointed out earlier, it is necessary to insert a removable stylet into the cannula body to stiffen it sufficiently to be installed in a patient's body. Traditionally, the stylet has been inserted through the infusion lumen, so when the stylet is thereafter removed, there can result a backflowing of blood through and out of the cannula until the CPG delivery line is clamped off.

However, in accordance with the present invention, such a backflowing of blood is prevented.

In one aspect of the invention, described in connection with three embodiments shown in FIGS. 1A, 2A and 3A, respectively, a stylet lumen is provided in the cannula body that is separate from the infusion lumen and is dedicated to the receipt of a stylet. In FIGS. 1A and 1B, the stylet lumen 30 extends through the cannula body parallel to both the infusion lumen 18 and the drain lumen 20. A distal end of the stylet lumen is closed by a plug 32, whereas the opposite proximal end thereof is open.

Figure 5:
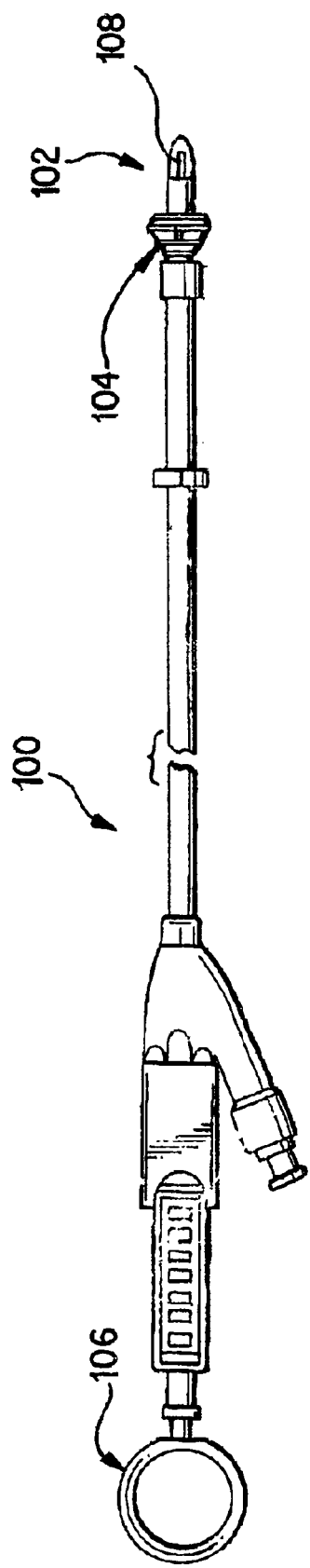
FIG. 5 is a side view of a prior art cannula.

In practice, the cannula 10 is inserted into a vessel of a patient, e.g., the coronary sinus of the heart, by inserting a stylet, such as the stylet 106 of FIG. 5, into the stylet lumen 30 in order to stiffen the cannula. After the distal end of the cannula has been inserted into the coronary sinus, the stylet is removed. There is no risk of blood traveling through the stylet lumen 30 as the stylet is removed, because the stylet lumen does not communicate with the coronary sinus (due to the presence of the plug 32). During this period, the infusion lumen is blocked-off by a cap or a clamp, or the infusion lumen is connected to a CPG delivery line prior to insertion of the cannula.

In the event that it becomes necessary, during the surgery, to reposition the cannula, that can be done by reinserting the stylet into the stylet lumen. There is no need to disconnect fluid-delivery conduits in order to do this, as would be the case if the stylet had to be inserted into the infusion lumen as has heretofore been the practice.

Figure 2A:
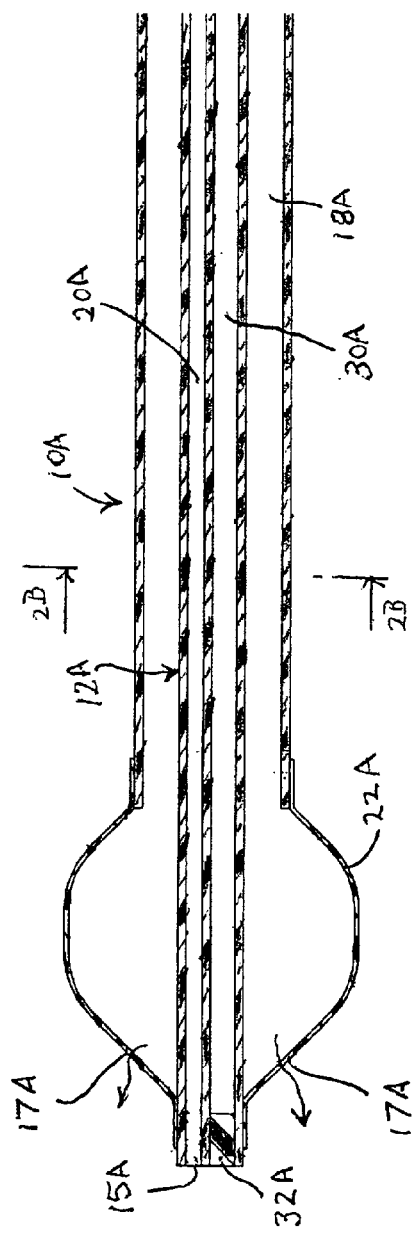
FIG. 2A is a longitudinal sectional view taken through a cannula along the line 2A—2A in FIG. 2B according to a second embodiment of the present invention.

A second embodiment of the invention, depicted in FIGS. 2A, 2B, is similar to that of FIGS. 1A, 1B and the reference numerals in those figures correspond to those of FIGS. 1A, 1B, but followed by the suffix "A". As in the case of FIGS. 1A, 1B, the cannula 10A is provided with a dedicated stylet lumen 30A. However, the cannula body 12A, instead of being of one-piece construction, comprises separate coaxial outer and inner shafts 12A', 12A". The stylet lumen 30A and the vent lumen 20A are formed in the inner shaft 12A", whereas an annulus 18A between the outer and inner shafts defines the infusion lumen and communicates directly with the interior of the balloon 22A. The balloon 22A includes outlet openings 17A for discharging CPG into the coronary sinus, as shown by the arrows. A distal or front end of the inner shaft (i.e., the left end in FIG. 2A) is joined to a distal end of the balloon 22A. A proximal, or rear, end of the inner shaft (not shown) could be anchored at its rear end, i.e., where a handle of the cannula is located. That rear end could be joined to the outer shaft or to the handle. Thus, the portion of the inner shaft located forwardly of the rear anchored end thereof is free to float laterally within the outer shaft. Otherwise, the operation of the cannula 10A is similar to that of the cannula 10 of FIGS. 1A, 1B.

FIGS. 3A, 3B depict a third embodiment of the invention, and the reference numerals thereof correspond to those of FIGS. 2A, 2B, but followed by the suffix B. As in the case of FIGS. 2A, 2B, the body 12B of the cannula 10B comprises coaxial outer and inner shafts 12B', 12B", but an annulus 19B disposed between those shafts is closed by an annular plug 34B disposed rearwardly of the balloon 22B. The outer shaft 12B' terminates within the balloon 22B, and the inner shaft extends therepast. A proximal end of the balloon is anchored to the outer shaft, and the distal end of the balloon is anchored to the inner shaft.

The vent lumen 20B, the infusion lumen 18B, and the dedicated stylet lumen 30B are formed in the inner shaft. The infusion lumen communicates with the balloon interior by way of communication passages 24B. The operation of the cannula 10B is similar to that of the earlier-described cannulae 10, 10A.

Figure 4B:
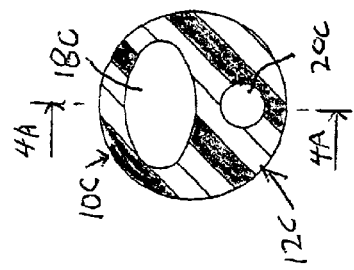
FIG. 4B is a cross sectional view taken through a cannula along the line 4B—4B in FIG. 4A.
Figure 4A:
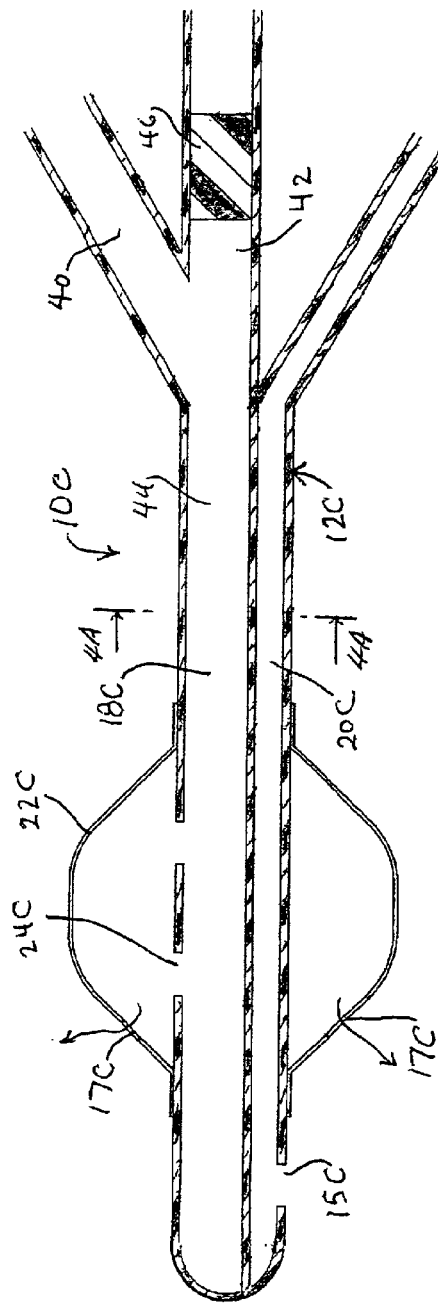
FIG. 4A is a longitudinal sectional view taken through a cannula along the line 4A—4A in FIG. 4B according to a fourth embodiment of the present invention.

In FIGS. 4A, 4B a fourth embodiment of the invention is disclosed, wherein the reference numerals correspond to those of FIGS. 1A, 1B but are followed by the suffix C. In this embodiment, there is disclosed a retrograde cannula 10C which does not possess a separate lumen dedicated to the stylet. Rather, an infusion lumen 18C is provided in a catheter body 12C which both conducts fluid (CPG) and receives the stylet. However, the lumen 18C has multiple inlets 40, 42. A first of the inlets 40 is a fluid inlet which extends at an angle to a main portion 44 of the infusion lumen 18C for introducing fluid (e.g., CPG) thereto.

A second of the inlets 42 is a stylet inlet which is preferably axially aligned with the infusion lumen main portion 44 for enabling a stylet to be inserted through the lumen 18C. Disposed in the second inlet 42 is a conventional self-sealing plug 46 formed of an elastic material capable of being penetrated by the stylet and then sealing closed after the stylet has been removed.

Thus, a stylet can be inserted into the lumen 18C to facilitate installation of the cannula within the patient's heart, and then removed without the risk of blood escaping rearwardly through the second inlet 42. That is, the first inlet 40 would be clamped closed and the second inlet 42 would be closed by the self-sealing plug 46.

After the cannula 10C has been installed, CPG can be administered to the patient by being conducted through: a CPG supply line (not shown), the fluid inlet 40, and the lumen 18C. Thereafter, the stylet can, if necessary, be reinserted through the lumen 18C to reorient the cannula without the need for disconnecting the CPG supply line as would be necessary if the fluid and the stylet were introduced through the same lumen inlet.

As in the earlier-described embodiments, the cannular body 12C includes a pressure-monitoring lumen 20C extending parallel to the lumen 18C.

Although the depicted preferred embodiments of retrograde cannulas are of the type having auto-inflate sealing members, the sealing members could alternatively be in the form of manual-inflate sealing members. The use of manual-inflate sealing members would require the provision of an inflation lumen in the cannula body for conducting inflation fluid to the sealing member.

In each of the embodiments disclosed herein, the CPG will be discharged into the coronary sinus through openings formed in the balloon. Alternatively, however, the cannulas 10, 10B, 10C could have an opening formed at a front or distal end of the infusion lumen in order to discharge the CPG.

In the embodiments disclosed in connection with FIGS. 2A–2B and 3A–3B, the inner shaft can be made axially movable relative to the outer shaft, whereby the balloon can be stretched to reduce the profile of the cannula.

Although the present invention has been described in connection with preferred embodiments thereof, it will be appreciated by those skilled in the art that additions, deletions, modifications, and substitutions not specifically described may be made without departing from the spirit and scope of the invention as defined in the appended claims.

What is claimed is:

1. A retrograde cannula for delivering fluid to a patient's vessel, the cannula having proximal and distal ends and including:
    an infusion lumen for conducting fluid to be discharged into the patient's vessel,
    a stylet lumen extending adjacent to the infusion lumen for receiving a stylet, a distal end of the stylet lumen being blocked, and
    an expandable sealing member disposed adjacent the distal end of the cannula for being expanded into sealing relationship with a wall of a vessel, the sealing member disposed in non-communication with the stylet lumen.

2. The retrograde cannula according to claim 1 wherein the sealing member constitutes an automatically inflatable balloon, the infusion lumen communicating with an interior of the balloon for inflating the balloon during the delivery of fluid through the infusion lumen.

3. The retrograde cannula according to claim 2 wherein the body includes an outer shaft and a coaxial inner shaft, the stylet lumen formed in the inner shaft.

4. The retrograde cannula according to claim 3 wherein the infusion lumen surrounds the inner shaft.

5. The retrograde cannula according to claim 3 wherein an annular space is formed between an outer periphery of the inner shaft and an inner periphery of the outer shaft, the annular space being blocked at a location proximal of the balloon.

6. The retrograde cannula according to claim 1 wherein the sealing member constitutes a manually inflatable balloon, the body further including an inflation lumen communicating with the interior of the balloon for supplying inflation fluid thereto.

7. The retrograde cannula according to claim 1 wherein the balloon includes a fluid outlet opening disposed in a front section thereof for discharging fluid received from the infusion lumen.

8. The retrograde cannula according to claim 1 wherein the body further includes a pressure-monitoring lumen extending therethrough.

* * * * *